United States Patent
Yuasa et al.

(10) Patent No.: US 11,091,720 B2
(45) Date of Patent: Aug. 17, 2021

(54) METHOD FOR PRODUCING PHOSPHOLIPID CONCENTRATE

(71) Applicant: MARUDAI FOOD CO., LTD., Osaka (JP)

(72) Inventors: Kouki Yuasa, Osaka (JP); Jun Kawamura, Osaka (JP); Satoshi Kotoura, Osaka (JP)

(73) Assignee: MARUDAI FOOD CO., LTD., Osaka (JP)

(*) Notice: Subject to any disclaimer, the term of this patent is extended or adjusted under 35 U.S.C. 154(b) by 0 days.

(21) Appl. No.: 16/970,234

(22) PCT Filed: Feb. 20, 2019

(86) PCT No.: PCT/JP2019/006419
§ 371 (c)(1),
(2) Date: Aug. 14, 2020

(87) PCT Pub. No.: WO2019/163856
PCT Pub. Date: Aug. 29, 2019

(65) Prior Publication Data
US 2021/0207055 A1    Jul. 8, 2021

(30) Foreign Application Priority Data
Feb. 21, 2018   (JP) .............................. JP2018-028964

(51) Int. Cl.
*C11B 1/10*      (2006.01)
*C11B 7/00*      (2006.01)
*C11B 3/00*      (2006.01)

(52) U.S. Cl.
CPC ............. *C11B 1/10* (2013.01); *C11B 3/006* (2013.01); *C11B 7/0075* (2013.01)

(58) Field of Classification Search
CPC .......... C11B 1/10; C11B 3/006; C11B 7/0075
See application file for complete search history.

(56) References Cited

U.S. PATENT DOCUMENTS 8,524,282 B2 *  9/2013  Nadachi .................... A23J 7/00
                                                        424/522
8,822,437 B2 *  9/2014  Ifuku ..................... A61K 31/685
                                                        514/114
(Continued)

FOREIGN PATENT DOCUMENTS

JP      H11-018688 A    1/1999
JP      2006-232967 A   9/2006
(Continued)

OTHER PUBLICATIONS

JP20100063406; (JP5483846), Motai Shiro et al., Functional material obtained from chicken breast meat and method for producing the same, English translation, 12 pages (Year: 2010).*

(Continued)

*Primary Examiner* — Yate' K Cutliff
(74) *Attorney, Agent, or Firm* — Paratus Law Group, PLLC

(57) ABSTRACT

This invention provides a technique that is capable of efficiently producing a phospholipid concentrate without using centrifugation and that is suitable for scaling up, the technique being for use in obtaining a phospholipid concentrate by subjecting an ethanol extract concentrate of bird breast meat to a degumming step and collecting gum. More specifically, the invention provides a method for producing a phospholipid concentrate, comprising a step of allowing a liquid mixture comprising an ethanol extract concentrate of bird breast meat and a 40 to 60 mass % aqueous ethanol solution in a mass ratio of 1:0.8 to 1.2 to stand at 40 to 60° C.

17 Claims, 4 Drawing Sheets

(56) References Cited

U.S. PATENT DOCUMENTS

2012/0283223 A1    11/2012  Ifuku et al.
2013/0172293 A1*   7/2013   Mawatari ................ A61P 29/00
                                                        514/76

FOREIGN PATENT DOCUMENTS

| | | | |
|---|---|---|---|
| JP | 2010-063406 A | 3/2010 | |
| JP | 2010-065167 A | 3/2010 | |
| JP | 2010063406 A * | 3/2010 | ............... A23L 1/30 |
| JP | 2016-210696 A | 12/2016 | |
| JP | 2017-200466 A | 11/2017 | |
| JP | 2017200466 A * | 11/2017 | ............... A23L 3/12 |
| WO | WO 2008/146942 A1 | 12/2008 | |
| WO | WO 2010/131718 A1 | 11/2010 | |
| WO | WO 2011/083827 A1 | 7/2011 | |
| WO | WO 2017/191838 A1 | 11/2017 | |

OTHER PUBLICATIONS

JP2017200466, Natatsu Yoshitake, et al., Chicken breast meat-derived Plasmalogen composition having improvement effects on cognitive function, preparation method thereof and processed foods for enhancing and/or improving cognitive function manufactured by adding the same, English translation 25 pages (Year: 2017).*

May 21, 2020, Japanese Office Action issued for related JP Application No. 2018-028951.

Satoshi Kotoura et al., Effects of Dietary Plasmalogens on Brain Function in the Healthy Subjects, Japanese Pharmacology and Therapeutics, 2017, pp. 1511-1521, vol. 45, No. 9.

* cited by examiner

METHOD FOR PRODUCING PHOSPHOLIPID CONCENTRATE

CROSS REFERENCE TO PRIOR APPLICATION

This application is a National Stage Entry of PCT International Patent Application No. PCT/JP2019/006419 (filed on Feb. 20, 2019) under 35 U.S.C. § 371, which claims priority to Japanese Patent Application No. 2018-028964 (filed on Feb. 21, 2018), each of which are hereby incorporated by reference in their entirety.

TECHNICAL FIELD

The present invention relates to a method for producing a phospholipid concentrate etc.

BACKGROUND ART

Phospholipids are important as constituents of living organisms. In particular, for example, plasmalogens are attracting attention as a functional material that has various effects such as enhancement of memory ability. For this reason, a method for efficiently preparing a phospholipid has been desired.

For example, methods for extracting components such as phospholipids from bird breast meat by ethanol extraction have previously been developed.

CITATION LIST

Patent Literature

PTL 1: JP2006-232967A
PTL 2: JP2010-63406A
PTL 3: JP2010-65167A
PTL 4: JP2016-210696A

SUMMARY OF INVENTION

Technical Problem

The present inventors attempted to extract useful components from bird breast meat with ethanol to concentrate phospholipids, i.e., types of components considered to be particularly important. In refining oil, it is usual practice to subject extracts from animals and plants to a degumming step to remove gum. However, phospholipids are components mainly contained in gum. Thus, to efficiently concentrate phospholipids, analysis was performed to concentrate ethanol extracts of bird breast meat, subject them to a degumming step, and collect gum precipitated by centrifugation.

Although this technique enabled concentration of phospholipids, expanding the production scale was difficult since this technique requires centrifugation as an essential step. Accordingly, development of a technique by which a phospholipid concentrate is efficiently produced without centrifugation has become necessary.

An object of the present invention is to provide a technique that is capable of efficiently producing a phospholipid concentrate without using centrifugation and that is suitable for scaling up, the technique being for use in obtaining a phospholipid concentrate by subjecting an ethanol extract concentrate of bird breast meat to a degumming step and collecting gum.

Solution to Problem

The present inventors found a possibility that the above problems can be solved by allowing a liquid mixture comprising an ethanol extract concentrate of bird breast meat and specific hydrous ethanol to stand under specific conditions. After conducting further improvements, the present inventors accomplished the present invention.

The invention encompasses, for example, the subject matter shown in the following items.

Item 1. A method for producing a phospholipid concentrate, comprising:
step (B) of allowing a liquid mixture comprising an ethanol extract concentrate of bird breast meat and a 40 to 60 mass % aqueous ethanol solution in a mass ratio of 1:0.8 to 1.2 to stand at 40 to 60° C.

Item 2. The method according to Item 1, wherein the standing time is 1 hour or more.

Item 3. The method according to Item 1 or 2, wherein the ethanol extract concentrate of bird breast meat has a water content of 1 mass % or less.

Item 4. The method according to any one of Items 1 to 3, further comprising, before step (B):
step (A) of mixing an ethanol extract concentrate of bird breast meat with a 40 to 60 mass % aqueous ethanol solution in a mass ratio of 1:0.8 to 1.2.

Item 5. The method according to any one of Items 1 to 4, further comprising, after step (B):
step (C) of collecting a lower layer from the liquid mixture separated into three layers, which are an upper layer, a middle layer, and a lower layer, after standing.

Item 6. The method according to Item 5, wherein the lower layer is collected by removing the upper layer and the middle layer, and the removal of the upper layer and the middle layer is performed by
(i) removing the upper layer from the liquid mixture separated into three layers, and allowing the resulting product to stand at a temperature of 10° C. or lower until the lower layer is gelled, followed by removal of the middle layer, or
(ii) allowing the liquid mixture separated into three layers to stand at a temperature of 10° C. or lower until the lower layer is gelled, followed by removal of the upper layer and the middle layer.

Item 7. The method according to any one of Items 1 to 6, wherein the bird breast meat is chicken breast meat.

Item 8. A method for producing a phospholipid concentrate, comprising:
step (b) of allowing a liquid mixture comprising an ethanol extract of bird breast meat, ethanol, and water to stand at 40 to 60° C., the liquid mixture having an ethanol content of 20 to 43.5 mass %.

Item 9. The method according to Item 8, wherein the liquid mixture has a water content of 16 to 36.5 mass %.

Item 10. The method according to Item 8 or 9, wherein the method satisfies at least one of the following features (α1) to (α5):
(α1): the standing time is 1 hour or more;
(α2): an ethanol extract concentrate of bird breast meat has a water content of 1 mass % or less;
(α3): after step (b), the method further comprises step (c) of collecting a lower layer from the liquid mixture separated into three layers, which are an upper layer, a middle layer, and a lower layer, after standing;
(α4): requirement (α3) is satisfied, the lower layer is collected by removing the upper layer and the middle layer, and the removal of the upper layer and the middle layer is performed by (i) removing the upper layer from the liquid mixture separated into three layers, and allowing the resulting product to stand at a temperature of 10° C. or lower until the lower layer is gelled, followed by removal of the middle layer, or
(ii) allowing the liquid mixture separated into three layers to stand at a temperature of 10° C. or lower until the lower layer is gelled, followed by removal of the upper layer and the middle layer; and
(α5): the bird breast meat is chicken breast meat.

Item 11. A method for concentrating phospholipids contained in bird breast meat, comprising:
step (B) of allowing a liquid mixture comprising an ethanol extract concentrate of bird breast meat and a 40 to 60 mass % aqueous ethanol solution in a mass ratio of 1:0.8 to 1.2 to stand at 40 to 60° C.

Item 12. The method according to Item 11, wherein the method satisfies at least one of the following features (α1) to (α5):
(α1): the standing time is 1 hour or more;
(α2): the ethanol extract concentrate of bird breast meat has a water content of 1 mass % or less;
(α3): after step (b), the method further comprises step (c) of collecting a lower layer from the liquid mixture separated into three layers, which are an upper layer, a middle layer, and a lower layer, after standing;
(α4): requirement (α3) is satisfied, the lower layer is collected by removing the upper layer and the middle layer, and the removal of the upper layer and the middle layer is performed by
(i) removing the upper layer from the liquid mixture separated into three layers, and allowing the resulting product to stand at a temperature of 10° C. or lower until the lower layer is gelled, followed by removal of the middle layer, or
(ii) allowing the liquid mixture separated into three layers to stand at a temperature of 10° C. or lower until the lower layer is gelled, followed by removal of the upper layer and the middle layer; and
(α5): the bird breast meat is chicken breast meat.

The above phrase "the method satisfies at least one of the following features (α1) to (α5)" means that the method satisfies at least one combination selected from all of the combinations of these five features. That is, it means any of 5!combinations.

Advantageous Effects of Invention

The method for producing a phospholipid concentrate, which is encompassed by the present invention, is capable of efficiently producing a phospholipid concentrate without using centrifugation and is suitable for scaling up, the method being for use in obtaining a phospholipid concentrate by subjecting an ethanol extract concentrate of bird breast meat to a degumming step and collecting gum.

DESCRIPTION OF EMBODIMENTS

Figure 1:
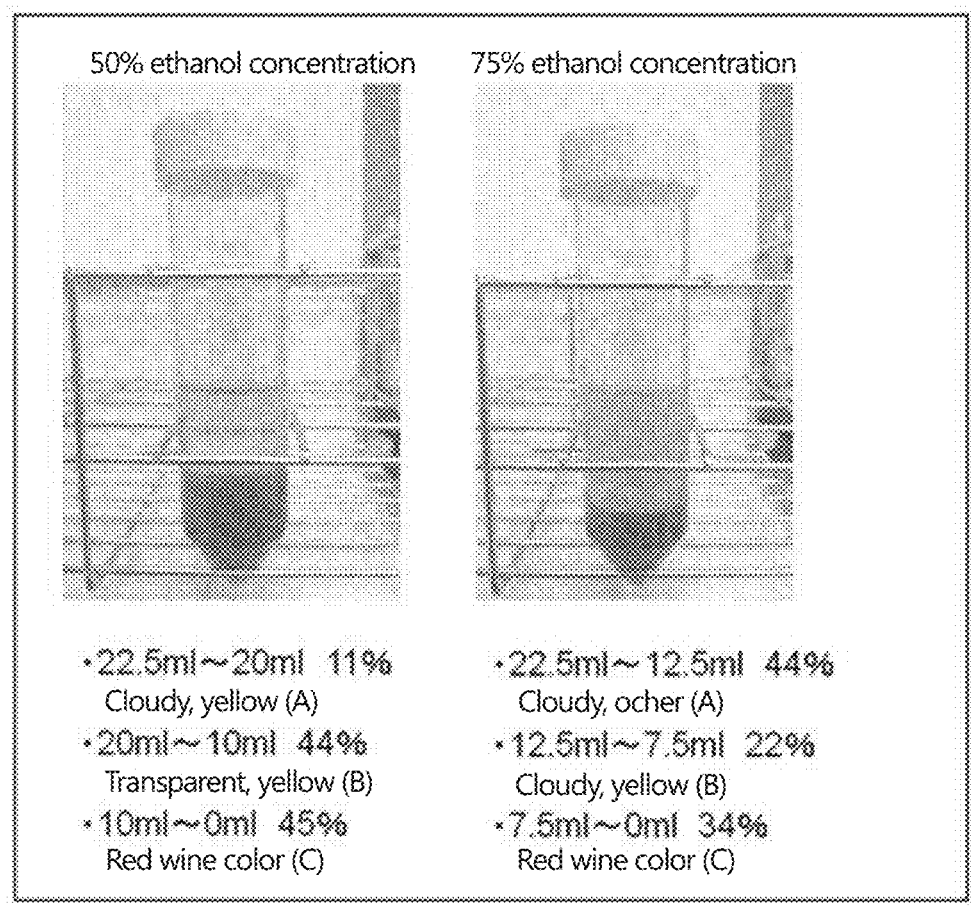
FIG. 1 is photographs showing the results obtained by mixing an ethanol extract concentrate of bird breast meat with an aqueous ethanol solution, and allowing the liquid mixture to stand and separate.

Below, each embodiment of the present invention is described in more detail.

The method for producing a phospholipid concentrate from bird breast meat, which is encompassed by the present invention (hereinafter sometimes referred to as "the method for producing a phospholipid concentrate of the present invention") comprises step (B) of allowing a liquid mixture comprising an ethanol extract concentrate of bird breast meat and a 40 to 60 mass % aqueous ethanol solution in a mass ratio of 1:0.8 to 1.2 to stand at 40 to 60° C.

In the present specification, the expression "mass %" denotes "w/w %" unless otherwise specified.

The bird breast meat is preferably breast meat of edible birds (e.g., chicken, domestic duck, Japanese quail, duck, green pheasant, and turkey), and particularly preferably chicken breast meat. The bird breast meat may be cut into an appropriate size. The meat may also be dried (in particular, freeze-dried).

The ethanol extraction method for bird breast meat is not particularly limited, and a known method, or a method that is easily conceivable from the known method, can be used. For example, extraction can be performed by adding ethanol in an amount of about 1 to 5 times that of bird breast meat, based on mass, followed by stirring or standing. The stirring or standing may be performed with heating. The heating may be performed, for example, at about 30 to 50° C. or about 35 to 45° C. Further, the stirring time or standing time is not particularly limited, and may be, for example, about 0.5 to 24 hours or about 1 to 12 hours. The obtained extract may be subjected to solid-liquid separation by filtration or the like, if necessary. Further, the extraction residue may be subjected to the same operation to obtain an extract again, which may be added to the extract obtained beforehand.

When the temperature is low (in particular, in winter), a deposit may be formed during the extraction process. The temperature at which a deposit is formed is not limited, and is specifically, for example, 10° C. or lower, 9° C. or lower, 8° C. or lower, 7° C. or lower, 6° C. or lower, 5° C. or lower, 4° C. or lower, 3° C. or lower, 2° C. or lower, 1° C. or lower, or 0° C. or lower. The deposit contains phospholipids; thus, if ethanol extraction is continued while the deposit is left as is, the phospholipids contained in the deposit will not be incorporated into the ethanol extracts. For this reason, the amount of phospholipids contained in the finally obtained phospholipid concentrate may vary. Therefore, when a deposit is formed, it is preferable to first perform heating to dissolve the deposit, or perform the step at a temperature at which no deposit is formed. When heating is performed to dissolve the deposit, the heating temperature is not particularly limited as long as the deposit dissolves and as long as it does not affect the quality. For example, the temperature is about 20 to 30° C. When the ethanol extraction step is performed at a temperature at which no deposit is formed, the step can be performed at a temperature of, for example, about 20 to 30° C.

The method of concentrating the obtained ethanol extract is not particularly limited, and a known method, or a method that is easily conceivable from the known method, can be used. Examples include vacuum concentration, heat concentration, and the like.

The concentration is preferably performed until the water content of the obtained ethanol extract concentrate is 1 mass % or less, more preferably 0.9 mass % or less, 0.8 mass % or less, 0.7 mass % or less, 0.6 mass % or less, or 0.5 mass % or less, and still more preferably 0.4 mass % or less, 0.3 mass % or less, or 0.2 mass % or less. The water content is a value determined by the Karl Fischer method.

The ethanol content of the obtained ethanol extract concentrate is preferably 15 mass % or less, and more preferably 14 mass % or less, 13 mass % or less, 12 mass % or less, 11 mass % or less, 10 mass % or less, 9 mass % or less, or 8 mass % or less. The ethanol content is a value obtained by subtracting the water content from the loss on drying determined by a dry-heat drying method (105° C., 3 hours). For example, when the loss on drying determined by dry heating is 90 mass %, and the water content is 1 mass %, the ethanol content is 100−90−1=9 (mass %).

An ethanol extract concentrate of bird breast meat and a 40 to 60 mass % aqueous ethanol solution are mixed in a mass ratio of 1:0.8 to 1.2. The lower limit of the mass ratio may be, for example, 1:0.85, 0.9, 0.95, or 1. The upper limit of the mass ratio may be, for example, 1:1.15, 1.1, 1.05, or 1. Further, the lower limit of the concentration of the aqueous ethanol solution used may be, for example, 41, 42, 43, 44, 45, 46, 47, 48, 49, or 50 mass %. The upper limit of the concentration of the aqueous ethanol solution used may be, for example, 59, 58, 57, 56, 55, 54, 53, 52, 51, or 50 mass %.

The thus-obtained liquid mixture is allowed to stand at 40 to 60° C. This allows the liquid mixture to separate into three layers (upper layer, middle layer, and lower layer), and phospholipids are concentrated in the lower layer.

The lower limit of the temperature for standing may be, for example, 41, 42, 43, 44, 45, 46, 47, 48, 49, or 50° C. The upper limit of the temperature for standing may be, for example, 59, 58, 57, 56, 55, 54, 53, 52, 51, or 50° C. The temperature for standing may vary within the above temperature range. However, the temperature is preferably as stable as possible. Even if the temperature changes, the range of change is preferably small (for example, within a range of about 1 to 5° C. or about 1 to 3° C.), and the rate of change is also preferably as slow as possible.

The standing time is not particularly limited as long as the liquid mixture separates into layers, and is preferably, for example, 1 hour or more. The time may be 2 hours or more, 3 hours or more, 4 hours or more, 5 hours or more, or 6 hours or more. The upper limit of the standing time is not particularly limited, and is, for example, 24 hours or less, 18 hours or less, 12 hours or less, or 10 hours or less.

As stated above, phospholipids are concentrated in the lower layer of the liquid mixture separated into three layers. Therefore, the method for producing a phospholipid concentrate of the present invention may further comprise a step of collecting the lower layer from the liquid mixture separated into three layers after standing.

The lower layer is collected, for example, by (i) removing the upper layer from the liquid mixture separated into three layers, and allowing the resulting product to stand at a temperature of 10° C. or lower until the lower layer is gelled, followed by removal of the middle layer, or (ii) allowing the liquid mixture separated into three layers to stand at a temperature of 10° C. or lower until the lower layer is gelled, followed by removal of the upper layer and the middle layer.

In both steps (i) and (ii), the temperature for standing is 10° C. or lower, and may be, for example, 9° C. or lower, 8° C. or lower, 7° C. or lower, 6° C. or lower, 5° C. or lower, or 4° C. or lower. Further, the standing time is not particularly limited as long as it is within the range in which the lower layer is formed into a gel, and is, for example, 12 hours or more.

Considering the above preferable range of the ethanol content of the ethanol extract concentrate as well, the liquid mixture comprising an ethanol extract concentrate of bird breast meat and a 40 to 60 mass % aqueous ethanol solution in a mass ratio of 1:0.8 to 1.2 can be interpreted to represent, for example, a liquid mixture comprising an ethanol extract of bird breast meat, ethanol, and water, and having an ethanol content of 20 to 43.5 mass %. The lower limit of the ethanol content of the liquid mixture may be 21, 22, 23, 24, 25, 26, 27, 28, 29, or 30 mass %. Further, the upper limit of the ethanol content of the liquid mixture may be 43, 42, 41, 40, 39, 38, 37, 36, 35, 34, or 33 mass %. Considering the above preferable range of the water content of the ethanol extract concentrate as well, the water content of the liquid mixture may be, for example, 16 to 36.5 mass %. The lower limit of the water content of the liquid mixture may be 17, 18, 19, 20, 21, 22, 23, or 24 mass %. Further, the upper limit of the water content of the liquid mixture may be 36, 35, 34, 33, 32, 31, 30, 29, 28, 27, or 26 mass %.

The present invention also encompasses a method for concentrating phospholipids contained in bird breast meat, comprising step (B) of allowing a liquid mixture comprising an ethanol extract concentrate of bird breast meat and a 40 to 60 mass % aqueous ethanol solution in a mass ratio of 1:0.8 to 1.2 to stand at 40 to 60° C. In this method, the same steps can be performed as in the above method for producing a phospholipid concentrate; thus, the same description as for the method for producing a phospholipid concentrate also applies to this method for concentrating phospholipids.

In the present specification, the term "comprising" and "containing" includes the meanings of "consisting essentially of" and "consisting of."

Examples

The present invention is described in more detail below. However, the present invention is not limited to the following Examples.

As the chicken breast meat, freeze-dried chicken breast meat (FD chicken breast meat) was used. The expression"%" denotes mass (w/w) % unless otherwise specified.

Ethanol Extraction

FD chicken breast meat (42 kg) was placed in an extraction tank. Then, 99% ethanol in an amount 4 times (w/v; 168 L) that of the FD chicken breast meat was placed in the extraction tank. After the tank was purged with nitrogen, the mixture was heated with stirring, and when the temperature reached 40° C., the mixture was allowed to stand for 90 minutes. After filtration through a 30-mesh filter, the extract was collected in a drum. The first extraction residue was placed in the extraction tank, and 99% ethanol in an amount 2.5 times (w/v; 105 L) that of the FD chicken breast meat was placed in the extraction tank. After the tank was purged with nitrogen, the mixture was heated with stirring, and when the temperature reached 40° C., the mixture was allowed to stand for 90 minutes. After filtration through a 30-mesh filter, the extract was collected in a drum. The extract was suction-filtered with 10S filter paper. The obtained liquid was used as an ethanol extract.

Concentration of Ethanol Extract Under Reduced Pressure

The ethanol extract was concentrated under reduced pressure at an internal temperature of 40° C. or lower to about the volume that could be entirely contained in a 50-L vat (about 8 kg). The resulting primary concentrated liquid was placed in a 50-L vat, and the pressure was reduced at an external temperature of 50 to 60° C. After the obtained concentrated liquid was filtered through a 30-mesh filter, the weight was measured. The weight was 5.12 kg. This concentrated liquid for use as an ethanol extract concentrate was stored at 4° C. until use.

The loss on drying of the ethanol extract concentrate was determined by a dry-heat drying method (105° C., 3 hours), while the water content was determined by the Karl Fischer method. The ethanol concentration was calculated by the subtraction method. As a result, the loss on drying was 8.05%, the water content was 0.15%, and the ethanol was 7.9%.

Study on Mixing of Ethanol Extract Concentrate and Aqueous Ethanol Solution

Study 1

To 15 g of the ethanol extract concentrate, an equivalent amount of 50, 60, 70, or 80% aqueous ethanol solution (w/w) was added, and the mixture was stirred at room temperature. After the mixture was allowed to stand at room temperature for 3 hours, the state of separation was confirmed.

Study 2

To 10 g of the ethanol extract concentrate, an equivalent amount of 25, 50, or 75% aqueous ethanol solution was added (w/w), and the mixture was heated with stirring until the temperature reached 50° C. After the mixture was allowed to stand at 50° C. for 3 hours, the state of separation was confirmed.

TLC Analysis

The components contained in the separated layers in each study were confirmed by thin-layer chromatography (TLC). More specifically, each layer separated in Study 1 and Study 2 was developed with a mobile phase (chloroform/methanol/water=65/25/4) using a thin layer made of a thin-layer plate (silica gel), and neutral lipids were separated from phospholipids. For the detection solution, 10% sulfuric acid was used.

In Study 1, when the 50% aqueous ethanol solution was mixed in the equivalent amount, the mixture became an emulsion, and separation could not be observed. When the 60, 70, or 80% aqueous ethanol solution was mixed in the equivalent amount, separation into two layers was observed. However, the lipid distribution of each layer in TLC confirmed insufficient separation since neutral lipids and phospholipids were present in both of these layers. These results clarified that the separation under room temperature conditions was insufficient.

Figure 2:
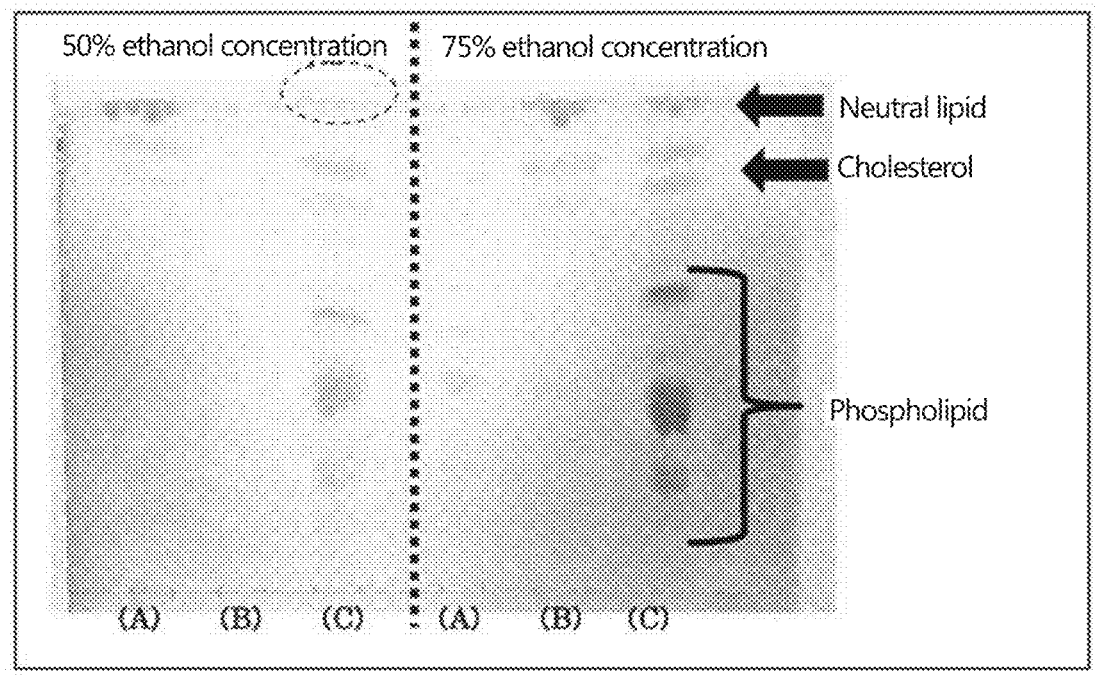
FIG. 2 shows the results of TLC analysis of each separated layer of FIG. 1.

In Study 2, when the 25% aqueous ethanol solution was mixed in the equivalent amount, the mixture became an emulsion, and separation could not be observed. However, when the 50 or 75% aqueous ethanol solution was mixed in the equivalent amount, separation into three layers was observed (FIG. 1). TLC analysis revealed that when the 75% ethanol was mixed in the equivalent amount, the lower-layer fraction containing the largest amount of phospholipids also contained large amounts of neutral lipids and cholesterol. In contrast, when the 50% aqueous ethanol solution was mixed in the equivalent amount, it was confirmed that neutral lipids were mainly present in the upper layer while phospholipids were mainly present in the lower layer (FIG. 2). In FIG. 2, (A) represents the upper layer, (B) represents the middle layer, and (C) represents the lower layer.

The above results revealed that when a 50% aqueous ethanol solution was mixed in an equivalent amount, and the mixture was allowed to stand at 50° C., a phospholipid concentrate was efficiently obtained from the ethanol extract concentrate of bird breast meat even without centrifugation.

Additionally, when the mixture was stored at 4° C. in a state in which the mixture separated into three layers, only the upper and lower layers were solidified. By using this feature, it was possible to more efficiently collect the lower layer alone. More specifically, first, only the upper layer was removed by suction from the mixture separated into three phases, and the resulting product was allowed to stand overnight at 4° C. Thereafter, the middle layer (liquid) and the lower layer (gel) were separated by solid-liquid separation to thus easily collect the lower layer alone.

Figure 3:
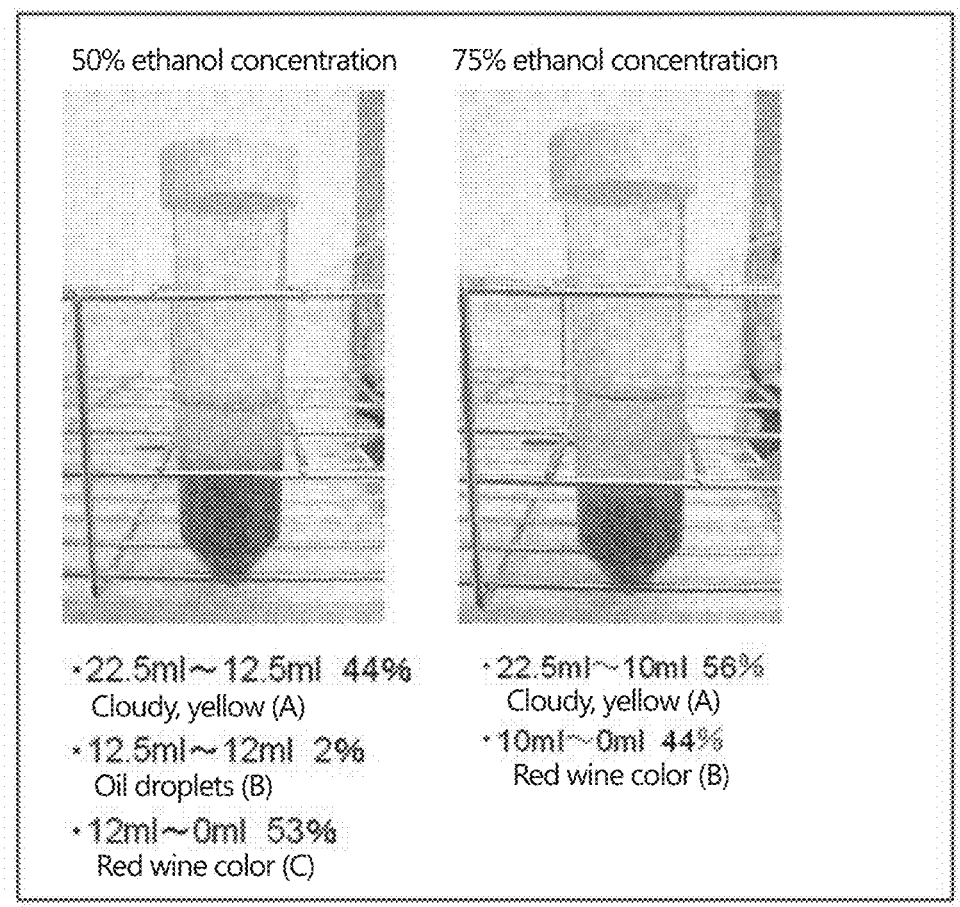
FIG. 3 is photographs showing the results obtained by mixing an ethanol extract concentrate of chicken gizzard with an aqueous ethanol solution, and allowing the liquid mixture to stand and separate.
Figure 4:
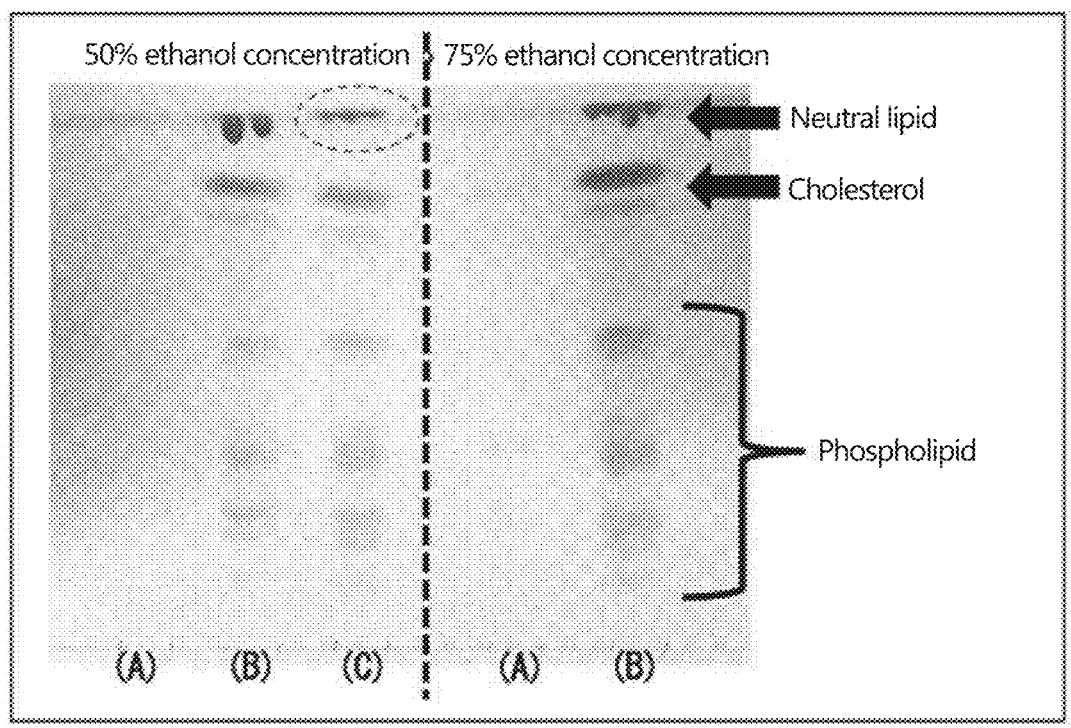
FIG. 4 shows the results of TLC analysis of each separated layer of FIG. 3.

A similar study (ethanol extraction, concentration of the ethanol extract, and mixing and standing of the ethanol extract concentrate and aqueous ethanol solution) was conducted using chicken gizzard or chicken skin instead of chicken breast meat. The results confirmed insufficient separation of neutral lipids from phospholipids. FIG. 3 shows the results obtained by mixing an ethanol extract concentrate of chicken gizzard and an aqueous ethanol solution, and allowing the mixture to stand and separate. FIG. 4 shows the results of TLC analysis of each separated layer of FIG. 3. In FIG. 4, in the 50% ethanol concentration (content), (A) represents the upper layer, (B) represents the middle layer, and (C) represents the lower layer, and in the 75% ethanol concentration (content), (A) represents the upper layer, and (B) represents the lower layer. (In the 75% ethanol concentration, the mixture separated into only two layers.)

These results clarified that this technique is particularly suitable for use with bird breast meat.

The invention claimed is:

1. A method for producing a phospholipid concentrate, comprising:
    step (B) of allowing a liquid mixture comprising an ethanol extract concentrate of bird breast meat and a 40 to 60 mass % aqueous ethanol solution in a mass ratio of 1:0.8 to 1.2 to stand at 40 to 60° C.

2. The method according to claim 1, wherein the standing time is 1 hour or more.

3. The method according to claim 1, wherein the ethanol extract concentrate of bird breast meat has a water content of 1 mass % or less.

4. The method according to claim 1, further comprising, before step (B):
    step (A) of mixing an ethanol extract concentrate of bird breast meat with a 40 to 60 mass % aqueous ethanol solution in a mass ratio of 1:0.8 to 1.2.

5. The method according to claim 1, further comprising, after step (B):
    step (C) of collecting a lower layer from the liquid mixture separated into three layers, which are an upper layer, a middle layer, and a lower layer, after standing.

6. The method according to claim 5, wherein the lower layer is collected by removing the upper layer and the middle layer, and the removal of the upper layer and the middle layer is performed by
    (i) removing the upper layer from the liquid mixture separated into three layers, and allowing the resulting product to stand at a temperature of 10° C. or lower until the lower layer is gelled, followed by removal of the middle layer, or
    (ii) allowing the liquid mixture separated into three layers to stand at a temperature of 10° C. or lower until the lower layer is gelled, followed by removal of the upper layer and the middle layer.

7. The method according to claim 1, wherein the bird breast meat is chicken breast meat.

8. A method for producing a phospholipid concentrate, comprising:
  step (b) of allowing a liquid mixture comprising an ethanol extract of bird breast meat, ethanol, and water to stand at 40 to 60° C., the liquid mixture having an ethanol content of 20 to 43.5 mass %.

9. The method according to claim 8, wherein the liquid mixture has a water content of 16 to 36.5 mass %.

10. The method according to claim 8, wherein the method satisfies at least one of the following features ($\alpha$1) to ($\alpha$4):
  ($\alpha$1): the standing time is 1 hour or more;
  ($\alpha$2): after step (b), the method further comprises step (c) of collecting a lower layer from the liquid mixture separated into three layers, which are an upper layer, a middle layer, and a lower layer, after standing;
  ($\alpha$3): requirement ($\alpha$2) is satisfied, the lower layer is collected by removing the upper layer and the middle layer, and the removal of the upper layer and the middle layer is performed by
    (i) removing the upper layer from the liquid mixture separated into three layers, and allowing the resulting product to stand at a temperature of 10° C. or lower until the lower layer is gelled, followed by removal of the middle layer, or
    (ii) allowing the liquid mixture separated into three layers to stand at a temperature of 10° C. or lower until the lower layer is gelled, followed by removal of the upper layer and the middle layer; and
  ($\alpha$4): the bird breast meat is chicken breast meat.

11. A method for concentrating phospholipids contained in bird breast meat, comprising:
  step (B) of allowing a liquid mixture comprising an ethanol extract concentrate of bird breast meat and a 40 to 60 mass % aqueous ethanol solution in a mass ratio of 1:0.8 to 1.2 to stand at 40 to 60° C.

12. The method according to claim 11, wherein the method satisfies at least one of the following features ($\alpha$1) to ($\alpha$5):
  ($\alpha$1): the standing time is 1 hour or more;
  ($\alpha$2): the ethanol extract concentrate of bird breast meat has a water content of 1 mass % or less;
  ($\alpha$3): after step (b), the method further comprises step (c) of collecting a lower layer from the liquid mixture separated into three layers, which are an upper layer, a middle layer, and a lower layer, after standing;
  ($\alpha$4): requirement ($\alpha$3) is satisfied, the lower layer is collected by removing the upper layer and the middle layer, and the removal of the upper layer and the middle layer is performed by
    (i) removing the upper layer from the liquid mixture separated into three layers, and allowing the resulting product to stand at a temperature of 10° C. or lower until the lower layer is gelled, followed by removal of the middle layer, or
    (ii) allowing the liquid mixture separated into three layers to stand at a temperature of 10° C. or lower until the lower layer is gelled, followed by removal of the upper layer and the middle layer; and
  ($\alpha$5): the bird breast meat is chicken breast meat.

13. The method according to claim 2, wherein the ethanol extract concentrate of bird breast meat has a water content of 1 mass % or less.

14. The method according to claim 13, further comprising, before step (B):
  step (A) of mixing an ethanol extract concentrate of bird breast meat with a 40 to 60 mass % aqueous ethanol solution in a mass ratio of 1:0.8 to 1.2.

15. The method according to claim 14, further comprising, after step (B):
  step (C) of collecting a lower layer from the liquid mixture separated into three layers, which are an upper layer, a middle layer, and a lower layer, after standing.

16. The method according to claim 15, wherein the lower layer is collected by removing the upper layer and the middle layer, and the removal of the upper layer and the middle layer is performed by
  (i) removing the upper layer from the liquid mixture separated into three layers, and allowing the resulting product to stand at a temperature of 10° C. or lower until the lower layer is gelled, followed by removal of the middle layer, or
  (ii) allowing the liquid mixture separated into three layers to stand at a temperature of 10° C. or lower until the lower layer is gelled, followed by removal of the upper layer and the middle layer.

17. The method according to claim 9, wherein the method satisfies at least one of the following features ($\alpha$1) to ($\alpha$4):
  ($\alpha$1): the standing time is 1 hour or more;
  ($\alpha$2): after step (b), the method further comprises step (c) of collecting a lower layer from the liquid mixture separated into three layers, which are an upper layer, a middle layer, and a lower layer, after standing;
  ($\alpha$3): requirement ($\alpha$2) is satisfied, the lower layer is collected by removing the upper layer and the middle layer, and the removal of the upper layer and the middle layer is performed by
    (i) removing the upper layer from the liquid mixture separated into three layers, and allowing the resulting product to stand at a temperature of 10° C. or lower until the lower layer is gelled, followed by removal of the middle layer, or
    (ii) allowing the liquid mixture separated into three layers to stand at a temperature of 10° C. or lower until the lower layer is gelled, followed by removal of the upper layer and the middle layer; and
  ($\alpha$4): the bird breast meat is chicken breast meat.

\* \* \* \* \*